United States Patent [19]

Melnyk

[11] 4,046,927

[45] Sept. 6, 1977

[54] PROCESS FOR SEMI-AUTOMATED PRODUCTION OF MAMMALIAN CELL SLIDES

[76] Inventor: John Melnyk, 1316 Cerritos Drive, Laguna Beach, Calif. 92651

[21] Appl. No.: 745,675

[22] Filed: Nov. 29, 1976

[51] Int. Cl.$^2$ .......................... C12B 3/00; C12B 9/00
[52] U.S. Cl. ...................................... 427/2; 128/1 R; 128/2 R; 195/1.8; 427/401
[58] Field of Search .................. 128/1 R, 2 R; 195/1.8; 427/2, 401

[56] References Cited

U.S. PATENT DOCUMENTS

| | | | |
|---|---|---|---|
| 3,065,669 | 11/1962 | Orsi | 195/1.8 X |
| 3,122,476 | 2/1964 | Gaeta | 195/1.8 |
| 3,249,504 | 5/1966 | Cappel et al. | 195/1.8 X |
| 3,687,806 | 8/1972 | Bovenkamp | 195/1.8 |

Primary Examiner—Michael R. Lusignan
Attorney, Agent, or Firm—John Joseph Hall

[57] ABSTRACT

A process for semi-automated production of mammalian cell slides, which includes dispensing suitable culture medium automatically in a plurality of containers in a culture tray, adding mammalian cells and incubating, removing the supernatant from the resulting cells simultaneously from the plurality of containers, adding hypotonic fluid simultaneously to the plurality of containers and following the treatment of hypotonic fluid by fixatives, collecting the resulting cell suspension in a dispenser manifold and discharging the cells on slides provided by a slide dispenser and spreading the cells in a cell spreader.

5 Claims, 1 Drawing Figure

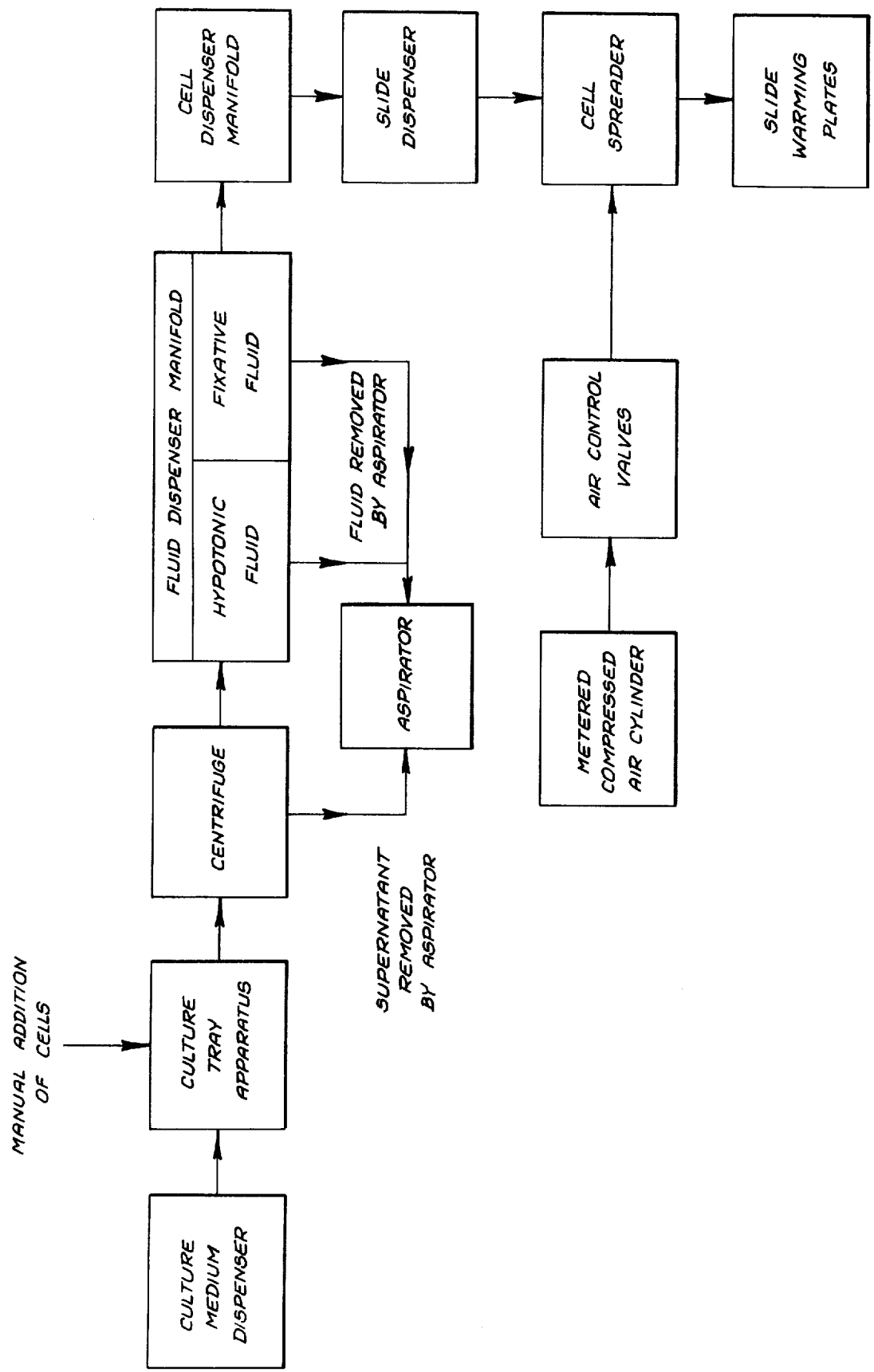

PROCESS FOR SEMI-AUTOMATED PRODUCTION OF MAMMALIAN CELL SLIDES

SUMMARY OF THE INVENTION

The process for semi-automated production of mammalian cell slides uses a plurality of culture tray means in which the mammalian cells are incubated together with a suitable medium. After a suitable period of time for incubation, such as 72 hours, the mixture of culture medium and mammalian cells are centrifuged while still in the culture tray means. The supernatant resulting from the centrifugation is removed simultaneously from the plurality of culture cell means. Hypotonic fluid is added simultaneously from a dispenser manifold to the cells remaining in the plurality of culture tray means. The hypotonic fluid is removed by aspiration and fixatives are added simultaneously from a dispenser manifold to the treated cells in the plurality of culture tray means. The fixative treatment may be repeated two or three times as desired. The resulting cell suspension is then collected in a cell dispenser manifold by suction and then discharged drop-wise simultaneously from the manifold onto the surface of a plurality of slides.

Air blasts from a compressed air cylinder are directed through a cell spreader on the drops of cell suspension on the surface of the slides to spread the cells evenly over the slide surfaces. The slides are then warmed to facilitate spreading and drying of the cell suspension on the slides.

In this manner, a large number of slides may be processed in an 8-hour work day. This process will produce up to and over 10 times as many slides as the conventional tube method of culturing cells in test tubes or vials, which are handled manually and individually with fluid being added or removed manually with pipettes.

Cytogenetic analysis is coming to be used more and more widely in clinical and research areas for various types of studies and screening of human health problems. A great need exists for the rapid production of mammalian cell slides which is relatively simple, of high quality, and consistent reproducability.

It is, therefore, an object of my invention to provide a process for production of mammalian cell slides which is relatively simple in operation.

Another object of my invention is to provide a process for production of mammalian cell slides in quantities up to and more than 10 times the amount produced by conventional manual methods in a single work day.

A further object of my invention is to provide a process for production of mammalian cell slides of high quality.

A yet further object of my invention is to provide a process for production of mammalian cell slides which is easily reproducible with consistent results.

These and other objects will be more readily understood by reference to the following description and claims. The FIGURE illustrates a preferred sequence of steps of the process.

The following example is a preferred embodiment of the invention using a culture tray having 12 wells as containers for the culture medium and mammalian cells.

EXAMPLE 1

3 ml. of a suitable culture medium is added simultaneously by a medium dispenser to each of the 12 wells of the culture tray, in groups of four wells each. Thereafter, 0.07 ml. of whole blood is added manually to each well. The mixture is then incubated for about 72 hours at a suitable temperature. The incubation time may be varied from 48 hours to 96 hours without adverse results. The preferred temperature of incubation is 37° C., although this may vary plus or minus 1.5°.

The mixture is then centrifuged while still in the culture tray means in a conventional centrifuge with a special carrier for the culture tray means. The centrifugation is carried out at room temperature for a period of time of approximately 10 minutes. The centrifugation time may be varied plus or minus five minutes without adverse results.

After centrifugation, the supernatant is removed by a vacuum simultaneously from all 12 wells of the culture tray means with an aspirator having 12 needles or other means, one for each well of the culture tray means. The needles are then cleaned by ultrasonic sound from a sonicator, for immediate reuse.

Hypotonic fluid is then added to the cells remaining in each of the 12 wells of the culture tray means simultaneously from a fluid dispenser manifold having 12 needles or other means, one for each well. The fluid dispenser manifold is mounted on a shaker device which is operating while the fluid is being dispensed to resuspend the cells in the culture tray means and provides thorough mixing. The fluid dispenser is provided with means for varying the fluid flow from a single drop to a steady flow as desired. A slow flow of fluid is preferable to avoid excessive cell breakage. This example uses 0.075 molar potassium chloride solution as the hypotonic fluid but various conventional hypotonic fluids may be used.

The hypotonic fluid is then removed from the treated cells by an aspirator simultaneously from each of the 12 wells.

The cells are then treated in the culture tray means with a fixative fluid consisting of three parts of absolute alcohol and one part of glacial acetic acid. Various conventional fixatives may be substituted for this particular fixative without adverse results. The fixative is added from the fluid dispenser manifold with the 12 needles in the same manner as the hypotonic fluid and removed in the same manner. The fixative treatment may be repeated two or three times as desired. This example uses three treatments with the fixative preferably.

The treated and resuspended cells are then collected up into a cell dispenser manifold having four needles. The manifold is placed over a group of four wells of the culture tray means manually and the needles are then lowered into the cell suspension and the cell suspension is drawn up into the manifold in a predetermined amount. The manifold is then placed in a position over a group of four slides, each of the four needles being positioned above one of the slides. The manifold is then caused to release a drop of the cell suspension through each of the four needles onto the slides. The cell dispenser then moves the four slides to a position under a cell spreader device consisting of a source of compressed air through air control valves. A controlled blast of air spreads the drops of cell suspension over the surface of each of the glass slides. The compressed air comes from a metered compressed air cylinder provided with the air control valves.

After the spreading of the cell suspension on the slides, the slides are advanced to a position slide-warming plates which produce a temperature of 50° Centigrade on the cell suspension to promote better spreading and drying of the material. The temperature may be varied plus or minus 5° and the time of warming is preferably three minutes but this warming time may be varied plus or minus one minute without adverse results. A longer warming time will not cause any adverse effect.

In this manner, the process will produce up to and over 10 times as many slides as current conventional methods of culturing cells in test tubes or vials by manual methods.

Further, the process produces reproducible results and slides of high quality.

Although I have described my invention in detail with respect to the accompanying drawing illustrating a preferred embodiment of the invention in conjunction with the specification and claims, it is understood that numerous changes in the details of construction and arrangement of parts and components may be made and in the details of the steps of the process without departing from the spirit and the scope of the invention as hereinafter claimed.

I claim:

1. A process for semi-automated production of mammalian cell slides, comprising:

adding a suitable culture medium from a dispenser into a plurality of culture tray means;

adding mammalian cells to the culture medium;

incubating said cells in the culture medium for a suitable period of time and at a suitable temperature in said plurality of culture tray means;

centrifuging the mixture of culture medium and said cells while in said culture tray means to produce a supernatant;

removing the supernatant by aspirator means simultaneously from said plurality of culture tray means, leaving said cells in said culture tray means;

adding hypotonic fluid to said cells in said plurality of culture tray means simultaneously from a dispenser while at the same time initiating and maintaining shaking of said culture tray means;

removing said hypotonic fluid and adding a fixative fluid to said cells in said plurality of culture tray means simultaneously from a dispenser, while at the same time initiating and maintaining shaking of said culture tray means;

removing said fixative fluid and collecting the resulting cell suspension in a cell dispenser manifold;

discharging the cell suspension from said cell dispenser manifold simultaneously on a plurality of slides;

and spreading said cell suspension over the surfaces of said plurality of slides with an air blast.

2. A process according to claim 1 in which the slides are warmed for a suitable period of time after the cell suspension is spread.

3. A process according to claim 1 in which the fixative fluid is repeatedly added and removed by an aspirator three times from the mammalian cells.

4. A process according to claim 1 in which the incubation time varies from a minimum of 24 hours to a maximum of 96 hours.

5. A process according to claim 1 in which the incubation temperature is a minimum of 35.5° C to a maximum of 38.5° C.

* * * * *